(12) United States Patent
Gaitas

(10) Patent No.: US 8,897,856 B2
(45) Date of Patent: Nov. 25, 2014

(54) ATHEROSCLEROSIS THERAPY VIA DELIVERY AND LOCALIZED HEATING OF MICRO SIZE PARTICLES

(71) Applicant: Angelo Gaitas, Ann Arbor, MI (US)

(72) Inventor: Angelo Gaitas, Ann Arbor, MI (US)

(73) Assignee: Angelo Gaitas, Miami, FL (US)

( * ) Notice: Subject to any disclaimer, the term of this patent is extended or adjusted under 35 U.S.C. 154(b) by 67 days.

(21) Appl. No.: 13/673,165

(22) Filed: Nov. 9, 2012

(65) Prior Publication Data

US 2013/0172728 A1 Jul. 4, 2013

Related U.S. Application Data

(60) Provisional application No. 61/563,756, filed on Nov. 26, 2011.

(51) Int. Cl.
```
A61N 2/00      (2006.01)
A61M 5/00      (2006.01)
A61N 1/40      (2006.01)
A61K 41/00     (2006.01)
A61K 47/48     (2006.01)
A61K 49/18     (2006.01)
A61K 33/26     (2006.01)
```
(52) U.S. Cl.
CPC ............... *A61N 2/004* (2013.01); *A61M 5/007* (2013.01); *A61N 1/406* (2013.01); *A61K 41/0052* (2013.01); *A61K 47/48538* (2013.01); *A61K 49/1875* (2013.01); *A61K 33/26* (2013.01)
USPC ................................. 600/411; 600/12; 606/27

(58) Field of Classification Search
CPC ............. B01J 20/28009; B01J 20/2803; B01J 20/28023; B01J 20/28045; B01J 20/32; A61N 2/004; A61M 5/007
USPC ........................................ 600/411, 12; 606/27
See application file for complete search history.

(56) References Cited

U.S. PATENT DOCUMENTS

| | | | |
|---|---|---|---|
| 5,891,094 A * | 4/1999 | Masterson et al. | 604/113 |
| 2002/0193785 A1* | 12/2002 | Naghavi et al. | 606/28 |
| 2003/0229340 A1* | 12/2003 | Sherry et al. | 606/27 |
| 2007/0031515 A1* | 2/2007 | Stucky et al. | 424/724 |
| 2007/0191811 A1* | 8/2007 | Berglund | 604/509 |
| 2008/0275498 A1* | 11/2008 | Palmer et al. | 606/200 |
| 2011/0070662 A1* | 3/2011 | Porter et al. | 436/501 |
| 2011/0125181 A1* | 5/2011 | Brady et al. | 606/200 |
| 2012/0226093 A1* | 9/2012 | Creighton | 600/12 |
| 2013/0261013 A1* | 10/2013 | Baltzer et al. | 506/9 |

\* cited by examiner

Primary Examiner — Baisakhi Roy

(57) ABSTRACT

The present invention relates generally to the treatment of atherosclerosis and thrombosis. Specifically, the invention relates to a method for removing vascular deposits by locally heating plaque sites with micron size particles that are administered intravenously and are heated inductively.

21 Claims, 9 Drawing Sheets

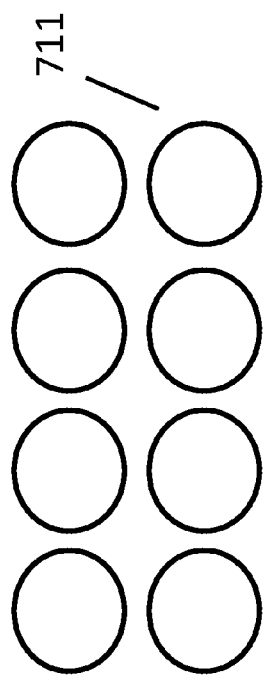
FIG. 8 (a)
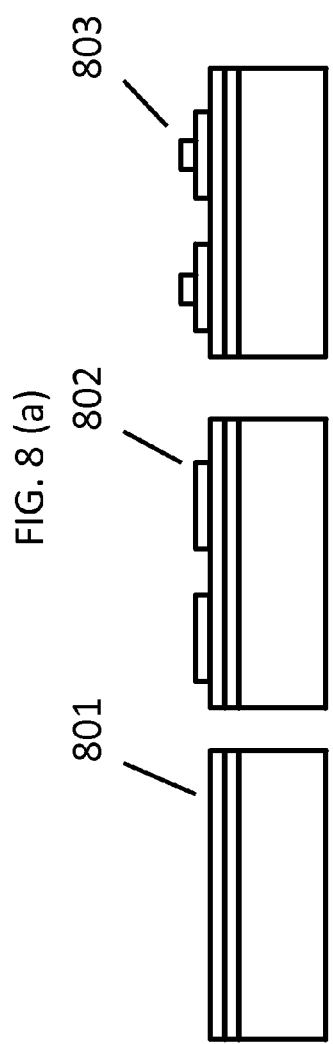
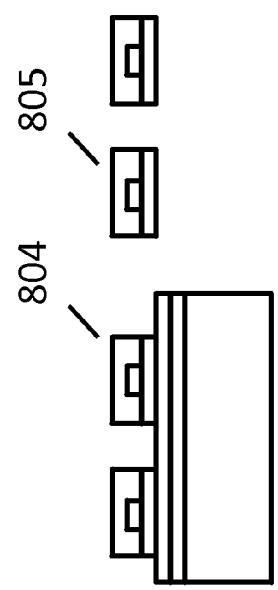
FIG. 8 (b)

ATHEROSCLEROSIS THERAPY VIA DELIVERY AND LOCALIZED HEATING OF MICRO SIZE PARTICLES

CROSS-REFERENCE TO RELATED DEVICE AND METHOD

The present application claims the benefit of U.S. Provisional Application No. 61/563,756, entitled "Atherosclerosis therapy via delivery and localized heating of micro size particles", filed on Nov. 28, 2011, which is hereby incorporated by reference herein in its entirety.

FIELD OF THE INVENTION

The present invention relates generally to the treatment of atherosclerosis and thrombosis. Specifically, the invention relates to a method for removing vascular deposits by locally heating plaque sites with micron size particles that are administered intravenously and are heated inductively.

BACKGROUND OF THE INVENTION

Atherosclerosis and thrombosis, such as coronary atherosclerosis, is a leading cause of death. Prevention and treatment of atherosclerosis continues to fall short. In atherosclerosis chronic inflammation of the arterial wall in caused by the buildup of macrophages, low density lipoproteins (LDL), foam cells, cholesterol, platelets, and other particles that form atheromatous plaque. Following plaque formation, stenosis and aneurysm occur. Eventually plaque may rupture causing acute coronary events.

Therefore there is a need in the art for an arthrosclerosis treatment that can break up such vascular deposits. These and other features and advantages of the present invention will be explained and will become obvious to one skilled in the art through the summary of the invention that follows.

SUMMARY OF THE INVENTION

Accordingly, it is an object of present invention to provide a method for removing vascular deposits using micron sized particles along with inductive heating. Embodiments of the proposed therapy can target any step of the atherogenesis. This invention can be used for any type of thrombosis such as venous thrombosis, deep vein thrombosis, portal vein thrombosis, renal vein thrombosis, jugular vein thrombosis, Budd-Chiari syndrome (hepatic vein or the inferior vena cava), Paget-Schroetter disease, cerebral venous sinus thrombosis, arterial thrombosis, atrial fibrillation, stroke, myocardial infarction, hepatic artery thrombosis, arterial embolus in the limbs.

According to an embodiment of the present invention, a method for the treatment of vascular deposits via the localized application of heat to said vascular deposits includes the steps of: selecting conductive particles ranging in size between 1 micron and 200 micron; attaching one or more biological binders to said conductive particles; wherein said one or more biological binders will cause said conductive particles to bind a vascular deposit; administering said conductive particles to a patient, wherein said conductive particles enter said patient's circulatory system; allowing said conductive particles to bind to said vascular deposit; heating said conductive particles, wherein said conductive particles are inductively heated via an alternating magnetic field; reducing said vascular deposit, wherein in said vascular deposit is reduced by inductively heating said conductive particles bound to said vascular deposit.

According to an embodiment of the present invention, the conductive particles include an outer insulating layer.

According to an embodiment of the present invention, the conductive particles are magnetic.

According to an embodiment of the present invention, the conductive particles are administered with an intravenous needle.

According to an embodiment of the present invention, the method further includes the step of extracting said conductive particles from said patient via an extraction area, wherein a magnet is placed at said extraction area causing said conductive particles to aggregate at said extraction area.

According to an embodiment of the present invention, the conductive particles are inductively heated for 15 minutes at 41-43 degrees centigrade to cause apoptosis.

According to an embodiment of the present invention, the method further includes the step of monitoring said vascular deposits, wherein said conductive particles are used for monitoring said vascular deposits with magnetic resonance imaging (MRI) contrast enhancement.

According to an embodiment of the present invention, the conductive particles have at least one of said one or more biological binders attached for rolling adhesion and at least one of said or one or more biological binders attached for stationary adhesion.

According to an embodiment of the present invention, the conductive particles are micro-fabricated with a manufacturing method selected from a group of manufacturing methods consisting of electric discharge machining, photo-etching, surface micromachining, and bulk micromachining.

According to an embodiment of the present invention, the conductive particles are comprised of a polymer bottom layer, a middle conductive layer, and a top polymer layer.

According to an embodiment of the present invention, the one or more biological binders is selected from a group of one or more biological binders consisting of antibodies, proteins, and ligands.

According to an embodiment of the present invention, the polymer bottom layer and said top polymer layer are selected from a group of polymers consisting of parylene, polyimide, SU-8, and PDMS.

According to an embodiment of the present invention, a method for the treatment of a clot via the localized application of heat includes the steps of: selecting particles ranging in size between 10 micron and 100 micron; attaching one or more biological binders to said particles, wherein said one or more biological binders will cause said particles to bind a clot; administering said particles to a patient, wherein said particles enter said patient's circulatory system; allowing said particles to bind to said clot; heating said particles, wherein said particles are inductively heated via an alternating magnetic field; and reducing said clot, wherein in said clot is reduced by inductively heating said particles bound to said clot.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

FIG. 8(a) is an illustration of an embodiment of a number of batch fabricated micron-sized particles and a fabrication process.

FIG. 8(b) is an illustration of an embodiment of a number of batch fabricated micron-sized particles and a fabrication process.

DETAILED DESCRIPTION OF THE INVENTION

Figure 1:
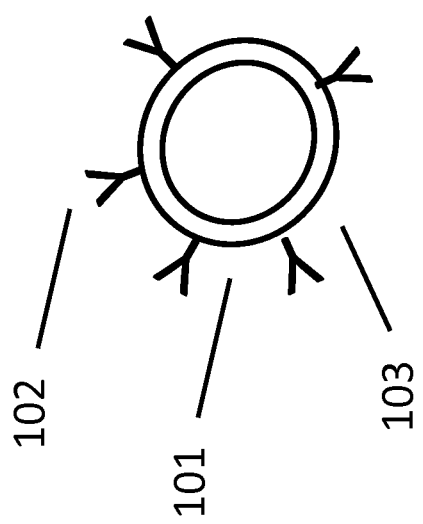
FIG. 1 is an illustration of an exemplary embodiment of a micron-sized particle that has attached on part of its exterior at least one type of a biological binder, such as ligand or antibody.

The present invention relates generally to the treatment of atherosclerosis and thrombosis. Specifically, the invention relates to a method for removing vascular deposits by locally heating plaque sites with micron size particles that are administered intravenously and are heated inductively.

According to an embodiment of the present invention, the method is used to treat and remove vascular deposits. In a preferred embodiment, this invention relates to a method for the treatment of atherosclerosis by locally heating plaque sites with micron size particles. In the preferred embodiment the particles will have a size between 1 micron and 200 micron. In an alternate embodiment the particles will range between 3 and 10 micron. In another alternate embodiment the particles are all one size or a specific size with a diameter variation of 1 micron, for example all the particles are 10 micron wide and 10 micron long. In another alternate embodiment the particles will range between 10 and 25 micron. In another alternate embodiment the particles will range between 5 and 25 micron. In a further alternate embodiment the particles will range between 25 and 50 micron. In certain embodiments, the particles may be as large as 100 micron. In other embodiments the particles may be similar in size to red blood cells. Finally, certain particles may not be uniform in length, width, or height. One of ordinary skill in the art would appreciate that the particles can be made effective in a variety of sizes, and embodiments of the present invention are contemplated for use with particles of any effective size.

In this disclosure the term vascular deposit, including its pluralized form, refers to, and may be used interchangeably with, any type of blockage, obstruction, build-up, or accumulation of matter that occurs throughout the circulatory system, including, but not limited to, plaque, fat, cholesterol, and blood clots. One of ordinary skill in the art would appreciate that there are materials that might form vascular deposits, and embodiments of present invention include any such material that might form a vascular deposit.

In this disclosure the term biological binder, including its pluralized form, refers to, and may be used interchangeably with, any type of material, including, but not limited to ligands, antibodies, aptamers, streptavidin, peptides and proteins. These materials can move throughout the body and the circulatory system and bind to and mark vascular deposits. One of ordinary skill in the art would appreciate that there are materials that might be used as a biological binder, and embodiments of present invention include any such material that might be suitable as a biological binder.

According to an embodiment of the present invention, the conductive particles are administered to the patient so that the particles enter the circulatory system of the patient. In a preferred embodiment the particles are injected intravenously via a hypodermic needle. In an alternate embodiment, the particles are swallowed by the patient. One of ordinary skill in the art would appreciate there are numerous ways to administer the particles to a patient, and embodiments of the present invention are contemplated for use with any such mode of administration.

According to an embodiment of the present invention, the conductive particles are heated inductively to reduce the size of vascular deposits. In a preferred embodiment, the conductive particles are heated with an external alternating magnetic field. One of ordinary skill in the art would appreciate that there are numerous methods through which the conductive particles could be heated, and embodiments of the present invention are contemplated for use with any such method.

Turning now to FIG. 1, an exemplary embodiment of a particle with an attached biological binder is shown. In this embodiment a particle 101 has attached on part of its exterior at least one type of biological binder 102 that will bind to one of the substances that make up vascular deposits such as fat, platelets (thrombocytes), cholesterol, fibrin, or other substances. Additionally, the particle has a coating on its exterior 103.

According to a preferred embodiment of the present invention, the reduction of vascular deposits can be achieved by heating or other means. In a preferred embodiment, a method for reducing vascular deposits is claimed where inductive heating is used to locally reduce vascular deposits by heating vascular deposits at relevant temperatures and causing cell apoptosis or cell death to those cells that make up the vascular deposits. The preferred embodiment is achieved by tagging particles with a biological binder that bind to plaque matter. As the particles flow in the body and the blood stream they will bind to the relevant locations where vascular deposits are located. In one embodiment an inductor is used outside of the body to locally heat the particles by heat induction.

According to embodiment of the present invention, heating of plaque for roughly 15 minutes at temperatures of 41-42° C. causes the cells of vascular deposits to rupture and die (apoptosis) reducing the vascular deposit.

According to an embodiment of the present invention, a patient is administered micro-size particles. The micro-size particles have attached to them biological binders that target and bind to vascular deposits matter shown in FIG. 1.

In this disclosure the terms conductive particles, electrically conducting particles, micro-size particles, microparticles, beads, micro-beads, particles, microspheres, spheres are used interchangeably. According to an embodiment of the present invention, the micro-size particles are made of any conductive material that can be inductively heated. In a preferred embodiment, these include but are not limited to: metals, semimetals, metal oxides (iron oxide, $Fe_3O_4$, ferrite, oxyhydroxides, Co oxides, NiO), meagnetic alloys (Fe—Co, Fe—Ni, Fe—Pt, Co—Pt), magnetic materials, metallic materials, paramagnetic materials, superparamagnetic materials, ferromagnetic materials, conductive polymers, intrinsically conducting polymers (ICPs). Examples of particles include: super-paramagnetic iron oxide, paramagnetic iron oxide particles, metallic particles of Ni (nickel), Co, Fe, FeCo, gold, and magnetite albumin microspheres. Other materials may be used such as perfluorocarbon particles that may be coated with metallic or magnetic material. Below several methods to fabricate these particles are described.

According to an embodiment of the present invention, biodegradable materials may be used as a material for the particles. In a preferred embodiment, these materials may include, but are not limited to, biodegradable plastics, biodegradable polythene film, synthetic biodegradable polymer. In the preferred embodiment, the biodegridible material is used as a coating of the conductive part of the particle. In another embodiment the entire particle is made of conductive biodegredible material (for example a mixture of polymeric and metallic particles or polymer with a conductive material). That way the particle will degrade after certain time in the body without a need for extraction leaving sub-micron parts that the body can easily dispose of. In another embodiment, the particles are made of a material that can be degraded when another material is injected in the blood stream. As an illustrative example, material A is a composite material made from B and C. C degrades in the presence of D. D is injected when the user wants to degrade A by destroying C. In another embodiment the particle degrades with heat, thus the particle in heated at a temperature to induce plaque reduction and then it is further heated at a more elevated temperature to dissolve. Alternatively, the material devolves if it is kept hot at a specific temperature for a specified period of time. In a preferred embodiment, the temperature could be the required temperature to reduce plaque or eliminate plaque or a higher temperature or a lower temperature. In yet another embodiment the particle melts and encapsulates the plaque matter to block it from accumulating and growing.

Prior art makes use of nanometer size particles. These are particles with dimensions less than 1000 nanometers. This disclosure is making use of micron size particles with dimensions larger than a micron. Micron size particles are less toxic as several studies have shown. Also due to their size (2-10 micron) they are comparable to cells therefore can heat a cell more effectively and rapidly. Larger particles will not be absorbed by cells, therefore are easier to filter out by the body through, for example, the blood stream. For instance recent studies from H. L. Karlsson et al. titled "Size-dependent toxicity of metal oxide particles—A comparison between nano- and micrometer size" reveal that "toxicological studies have shown increased toxicity of nanoparticles (<100 nm) compared to micrometer particles of the same composition, which has raised concern about the impact on human health from nanoparticles." In one embodiment the particles are 30 micron or larger. A limited number of larger than 30 micron particles are injected (for example 100 particles are injected). Thus making it easier for the body to eliminate them after treatment. In another embodiment the particles are 10 micron to 40 micron or all the particles are of the same size between 10 and 20 micron.

According to an embodiment of the present invention, attachment of biological binders such as antibodies to micro-particles can be done according to published literature.

Figure 2:
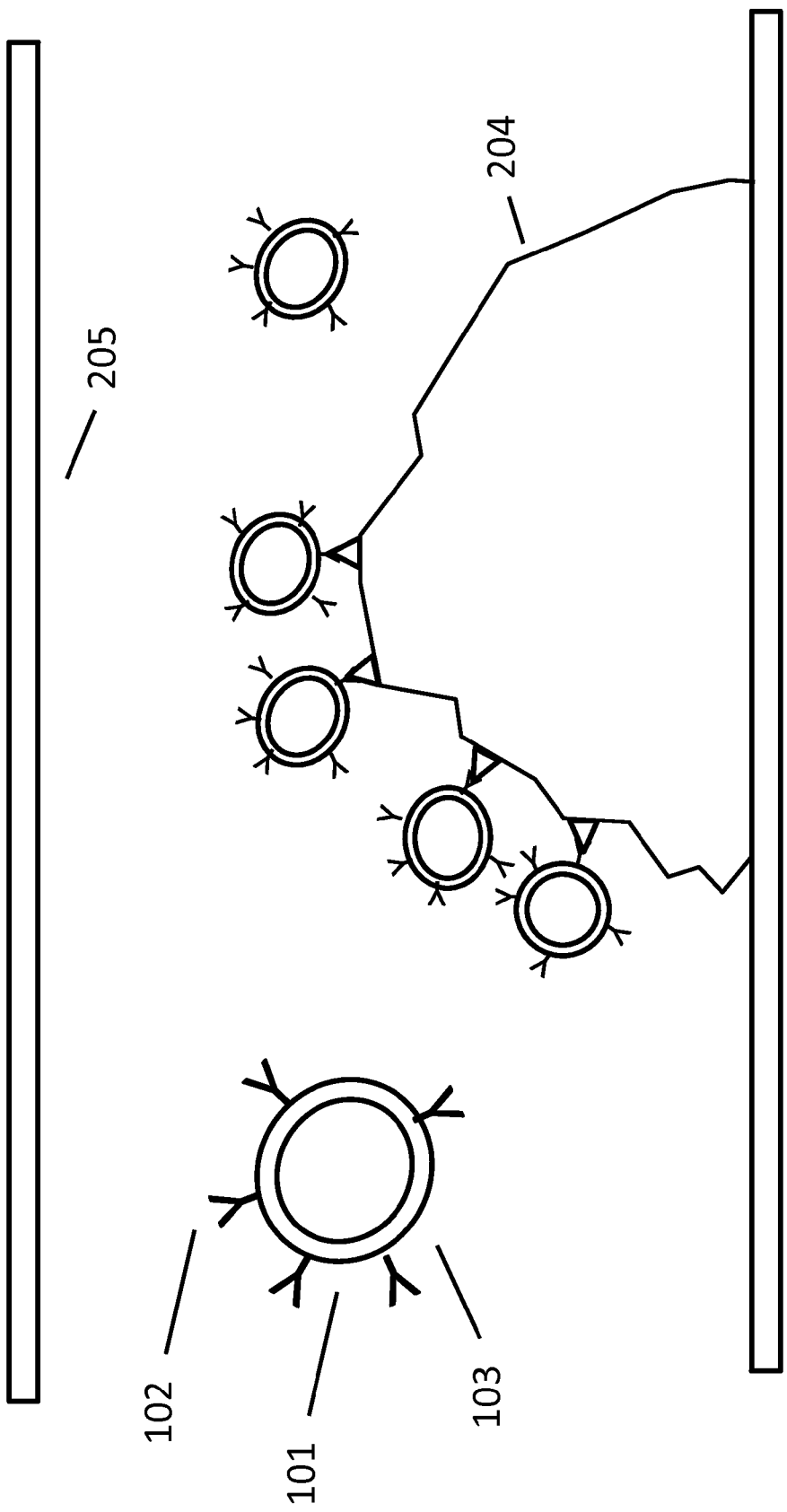
FIG. 2 is an illustration of an embodiment for reducing plaque build-up where inductive heating is used to locally reduce vascular deposits by heating the targeted vascular deposits at relevant temperatures.

Turning now to FIG. 2, an exemplary embodiment of micro-particles attaching to a vascular deposit. A number of biological materials that compose vascular deposits can be targeted as biomarkers. These include key components in the atherosclerotic process. For example targets may include macrophage cells, debris that contain lipids (cholesterol and fatty acids), calcium, cholesterol (low-density lipoprotein (LDL)), fibrous connective tissue, foam cells, thrombin, fibrin, macrophages, high density lipoproteins, $\alpha v\beta 3$ and $\alpha 5\beta 3$ integrin, and platelets. Examples include: Chimeric 7E3 antibody Fab (c7E3) fragment can selectively bind to glycoprotein IIb/IIIa integrin on platelet (Topol et al, Randomized trial of coronary intervention with antibody against platelet IIb/IIIa iritegrin for reduction of clinical restenosis: results at six months, Lancet 1994; 343: 881-86; pharmacycode.com/fda/7E3_antibody). Materials or targets such as Glycoprotein (GP) Iba and von Willebrand factor (vWF), aIIbb3, fibrinogen, integrins a2b1 and aIIbb3 (GP IIb-IIIa complex) can be used to coat particles or as targets of platelet thrombosis (Zaverio M. Ruggeri, Judith A. Dent, and Enrique Sald 'var; Contribution of Distinct Adhesive Interactions to Platelet; Blood, Vol 94, No 1 (July 1), 1999: pp 172-178). Glycoprotein receptors, von Willebrand Factor can be targeted with materials that will attach to them. Other proteins such as fibronectin, fibrinogen, thrombospondin, and laminin may also be used to coat the particle (Inhibitors of Platelet Adhesion, Todd L. Kiefer, Richard C. Becker, Circulation. 2009; 120:2488-2495). Aggregation in flowing blood. Integrin can be targeted with anti-B3-antibody. Antifibrin monoclonal antibodies may be used to target fibrin. Lipoprotein-associated phospholipase A2 (Lp-PLA2) can be targeted by coating the particle with monoclonal antibody clone 4B4 (diaDexus, South San Francisco, Calif.) (Frank D. Kolodgie, et al., "Lipoprotein-Associated Phospholipase A2 Protein Expression in the Natural Progression of Human Coronary Atherosclerosis", Arteriosclerosis, Thrombosis, and Vascular Biology, 2006; 26; 2523-2529). Human antibody L19 may also be used to target ED-B (Matter et al, Molecular Imaging of Atherosclerotic Plaques Using a Human Antibody Against the Extra-Domain B of Fibronectin, Circ. Res. 2004; 95; 1225-1233). Another candidate for a capture antibody is Apolipoprotein B (APOB or ApoB) that is the primary apolipoprotein of low-density lipoproteins (LDL). Apolipoprotein B occurs in two isoforms, APOB48 and APOB100. Other antibodies can be found in literature and include but are not limited to the following: Tobias von Lukowicz et al. J Nucl Med 2007; 48:582-587, DOI: 10.2967/jnumed.106.036046; Stefan G. Ruehm, et al., Magnetic Resonance Imaging of Atherosclerotic Plaque With Ultrasmall Superparamagnetic Particles of Iron Oxide in Hyperlipidemic Rabbits, Circulation, 2001; Itabe, et al. A Monoclonal Antibody against Oxidized Lipoprotein Recognizes Foam Cells in Atherosclerotic Lesions, The Journal of Biological Chemistry Vol 269 No 21 May 1994 p.p. 15274. In one embodiment the micro-particles are coated with antibodies or aptamers or other biological agents to prevent platelet adhesion, which causes atherosclerotic coronary artery disease (a partial list of target proteins, antibodies, and other biomolecules can be found in the following publication: "Todd L. Kiefer, MD, PhD; Richard C. Becker, MD, Inhibitors of Platelet Adhesion, Circulation. 2009; 120:2488-2495"). For example, the glycoprotein Ib/IX/V receptor complex that consists of four subunits that span the platelet cell membrane can be targeted. Other potential protein coatings or targets include: thromboxane A, adenosine diphosphate, thrombin, tissue factor, integrin, GP IIb/IIIa, fibrinogen, VWF, thrombin, fibrin.

According to an embodiment of the present invention, the surface of the particles is coated. In one preferred embodiment the coating is polar to prevent aggregation of particles. In an alternate preferred embodiment the coating is a highly charged coating, polyethylene glycol linked to terminal hydroxyl, or of methoxy groups, or of thiol groups. Thiolates (derived from thiols) form strong complexes with metals. The particle can be linked to biological binders that bind to vascular deposits such as monoclonal antibodies, aptamers, streptavidin or peptides. These biological binders are covalently linked to the particle. Multivalent coating with many target groups provide powerful attachment. Monovalent coating may also be used. Cells can be used for coating for example red blood cell or platelets attached to the particle.

According to an embodiment of the present invention, the particles are coated with self-assembled monolayers (SAMs). In a preferred embodiment these monolayers are made of two parts: the head and the tail. The SAMs head binds to the particle and the SAMs tail binds to the antibodies or aptamer or other biological binder that in turn binds to vascular deposits. Self-assembled monolayers (SAM) of organic molecules having a functional group with affinity to the particle's outer shell can be used. SAMs consist of a head group and a tail/functional end group. First, the head groups (including thiols, silanes, phosphonates, etc.) are absorbed on the particle's substrate in a vapor or liquid phase. For example thiol-metal bonds are used to attach organic molecules to gold thin films that can be deposited on the particle. The tail groups assemble away from the substrate. The tail groups have an affinity for cells, proteins, or molecules that are part of plaque. The substrate can be planar (silicon, metals etc.) or curved or of any shape. Examples of head groups that can be used are: alkanethiols, aromatic thiols, dithiol 1,4-Benzene-dimethanethiol, thiols, selenides, tellurides, silanes for non-metallic oxide surfaces. One method of producing SAMs is by immersing the particles in a solution (for example alkane thiol in ethanol) for a few minutes (example alkanethiolates) up to 72 hours.

Figure 3:
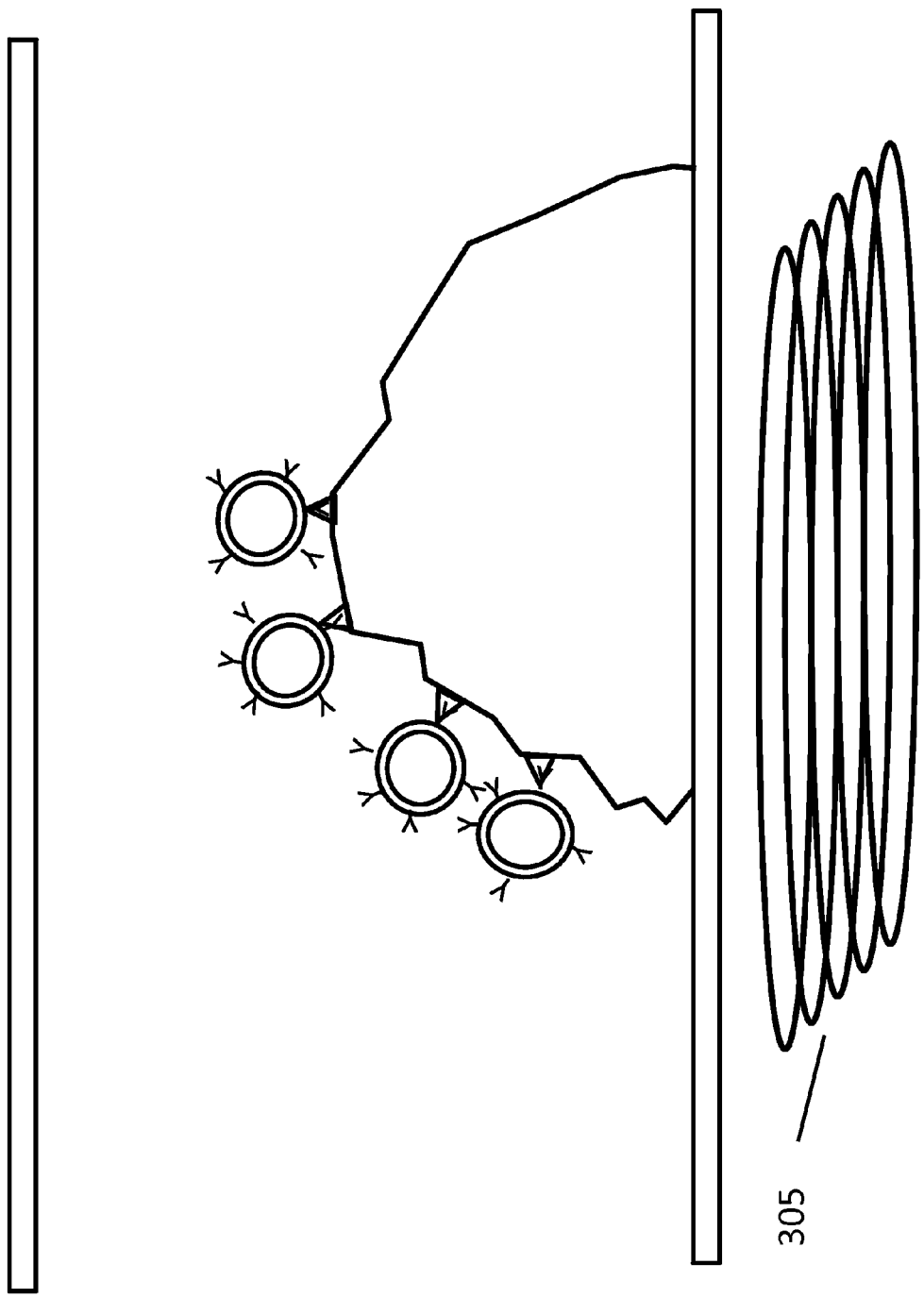
FIG. 3 is an illustration of an embodiment of micron-sized particles attached to vascular deposits in the presence of an alternating magnetic field.

Turning now to FIG. 3, an exemplary embodiment of micro-particles being inductively heated. In a preferred embodiment the particles are heated with an application of an external alternating magnetic field to inductively heat them. In induction heating an electrically conducting object, in this case a micron size particle, is heated by electromagnetic induction. Eddy currents are created on and within the particle leading to Joule heating. A high-frequency alternating current (AC) is passed through an electromagnet 305. In the preferred embodiment the electromagnet is an induction coil made of a metal wire such as copper. Examples of electromagnets, electromagnetic frequencies, and their values are: a) up to 400 kHz frequency and up to 6.5 kA/m amplitude of magnetic field, b) 15 kW power through the coil and up to 400 kHz frequency, c) 25-50 kHz frequency and 2 kA/m, d) frequency of about 400 kHz and amplitudes of about 10 kA/m, e) power up to 1.5 kW or up to 12 kW, field intensities up to 180 oersteds (14.3 kA/m), a coil 2½ inches in diameter, f) a portable coil capable of generating alternating magnetic fields of up to 3.5 MHz and up to 1.5 mT to heat up to 60.8 C temperatures; g) the frequency of the magnetic field is 62.1 kHz and the power is 2.2 kW.

According to an embodiment of the present invention, the particles are administered to the patient so that they may enter the body and the circulatory system. In a preferred embodiment the particles are mixed with liquid substances such as blood or saline or other liquid substances and administered by injection as an intravenous solution. Other injections include intramuscular, intraperitoneal, or intraosseous solution. In alternative embodiments, other administration methods include inhaling, insufflation, orally, as a liquid or solid, that is absorbed through the intestines, rectally, sublingually, diffusing into the blood through tissues under the tongue, and through a bolus placement.

According to an embodiment of the present invention, when sufficient time has passed allowing for the particles to attach to the plaque, the particles are inductively heated. In a preferred embodiment, heating vascular deposits achieves one of the following: melts certain particles that make up the plaque, causes cell apoptosis or cell death, causes cell lysis or membrane rupturing, or ablation by heating the targeted plaque cells and matter at relevant temperatures.

Figure 4:
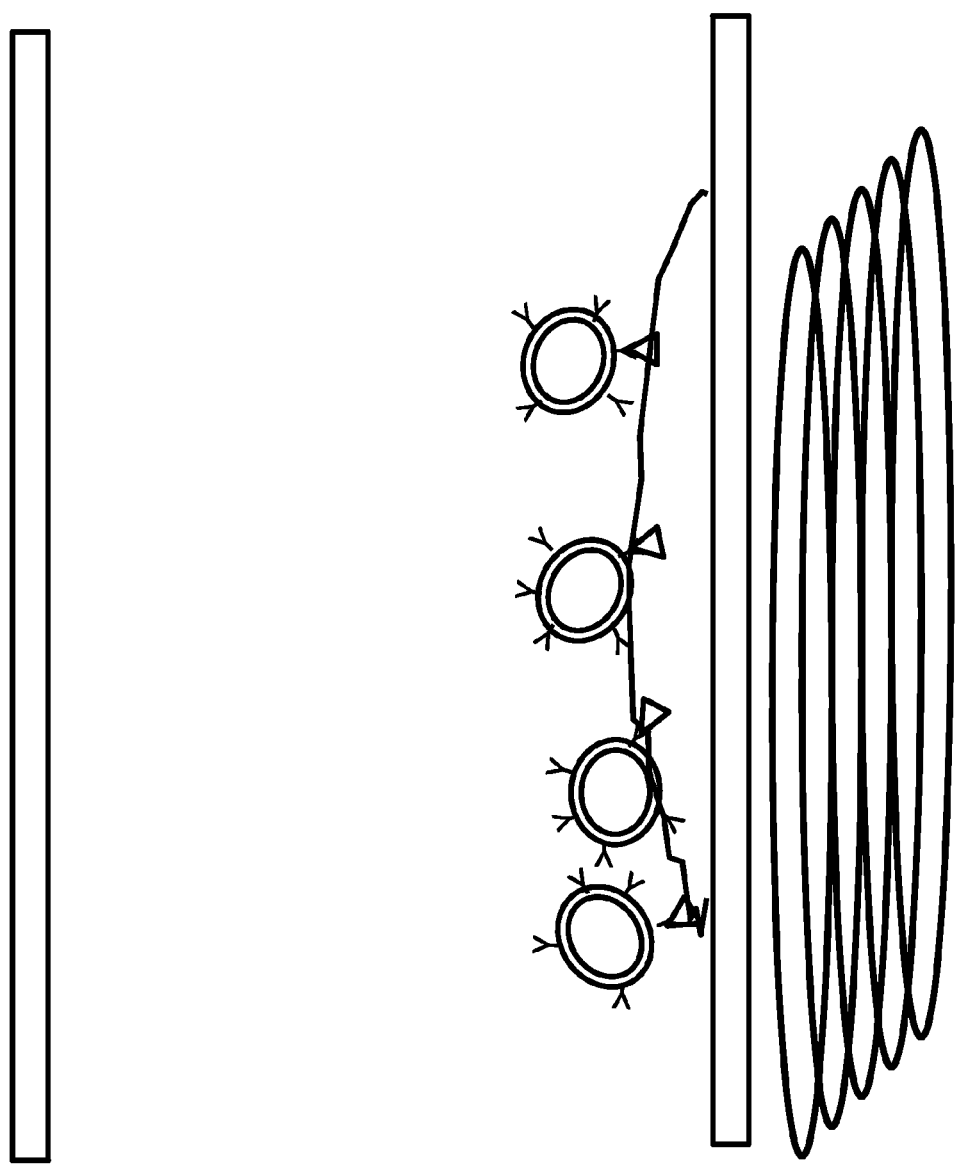
FIG. 4 is an illustration of an embodiment of reducing a vascular deposit by inductive heating.

Turning now to FIG. 4, an exemplary embodiment of a vascular deposit being reduced by inductive heating. In one embodiment atherosclerotic plaque is heated for about fifteen minutes at temperatures of 41-42° C. causing apoptosis, in which inflammatory plaque cells rupture and undergo death as shown. In another embodiment that particle is permanently stuck/attached to the wall of the artery where plaque is present for repeat therapies when plaque build-up re-occurs over time (for example 1 month after the first therapy). The same principle can be used for stents. If metal stents are used or metal stents coated with a bio-compatible polymer these could also be inductively heated over time to reduce plaque.

According to an embodiment of the present invention, heat may also be applied until melting or reduction of vascular deposit. In a preferred embodiment, the temperature could be as high as 148-150° C. (or any value up to 150° C.), which is the melting point of cholesterol. Alternatively, the temperature could be set to 80° C. for 10 seconds, then at body temperature and then back to 80° C. until plaque is reduced. In one alternate embodiment, the temperature can be lower than that to avoid causing cell death of near by cells. Other heating methods can be intermittent or heating can be repeated for a number of times. For example heating could last a few seconds or minutes to avoid damage to nearby healthy cells and tissue and could be repeated every 30 seconds for several times or until plaque is reduced. One of ordinary skill in the art would appreciate that there are many heating methods that would be acceptable to use in practicing this invention, and embodiments of the present invention are contemplated for use with any such heating method.

Conductive heating dominates in small scales. Studies (Merabia et al. "Critical heat flux around strongly-heated nanoparticles", Phys. Rev. E. Stat. Nonlin. Soft Matter Phys. 2009 February; 79) have shown that small sized particles can be heated inside fluids to very high temperatures and that the temperature gradient developed from the heated "particle drops to ambient temperature just one radius away from the particle surface". Therefore the temperature in the blood will not be significantly raised with heating.

Figure 5:
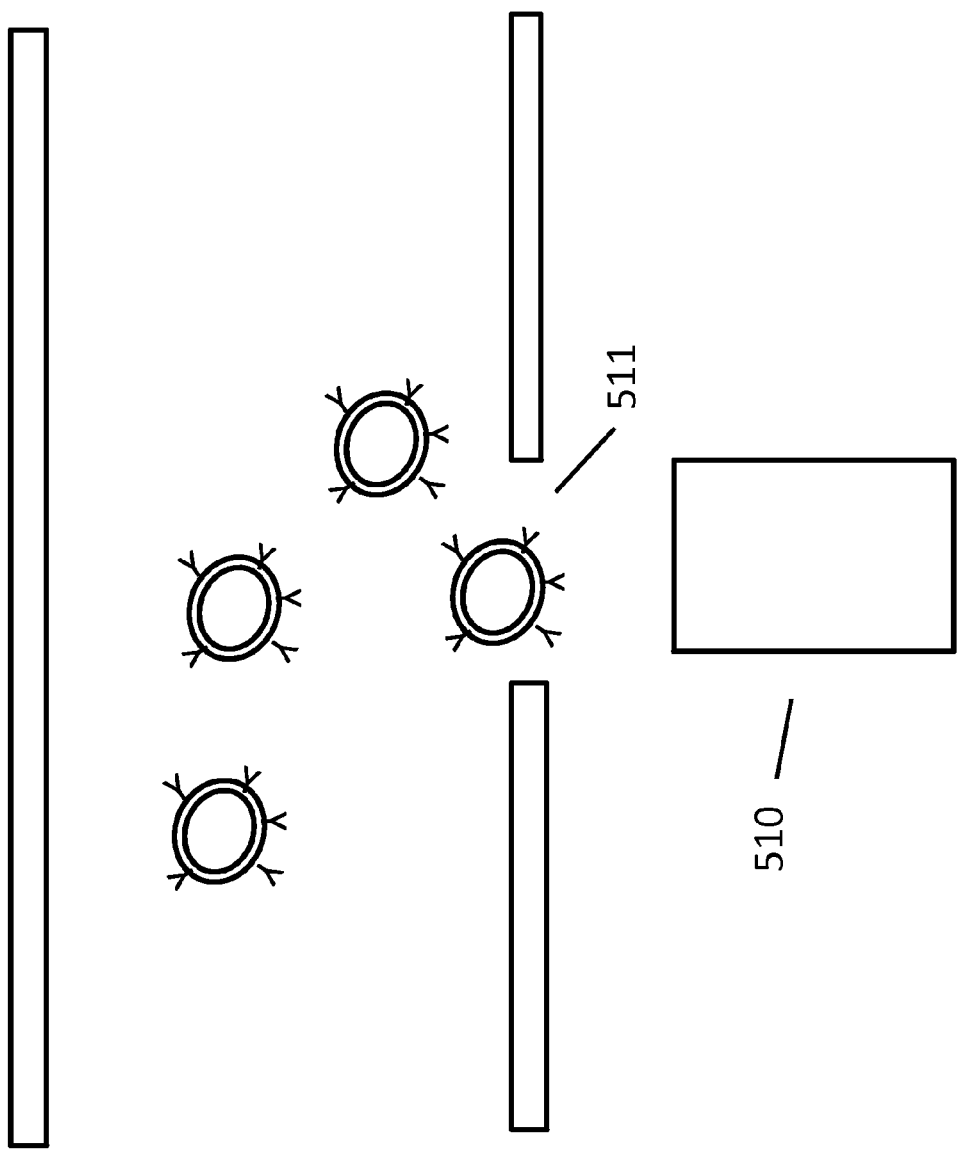
FIG. 5 is an illustration of an embodiment of a method for extracting the micron-sized particles from the body by bringing a magnet in close proximity so that the particles aggregate near the extraction area.

Turning now to FIG. 5, an exemplary embodiment for extracting the particles from the body. If the particles 511 are magnetic then after plaque reduction therapy, a magnet 510 with a strong magnetic field is used to concentrate the particles that are in the blood stream at a location where they are easily extractable. For instance the particles are extracted using a needle or a syringe. In one embodiment the syringe includes a movable magnet.

Figure 6:
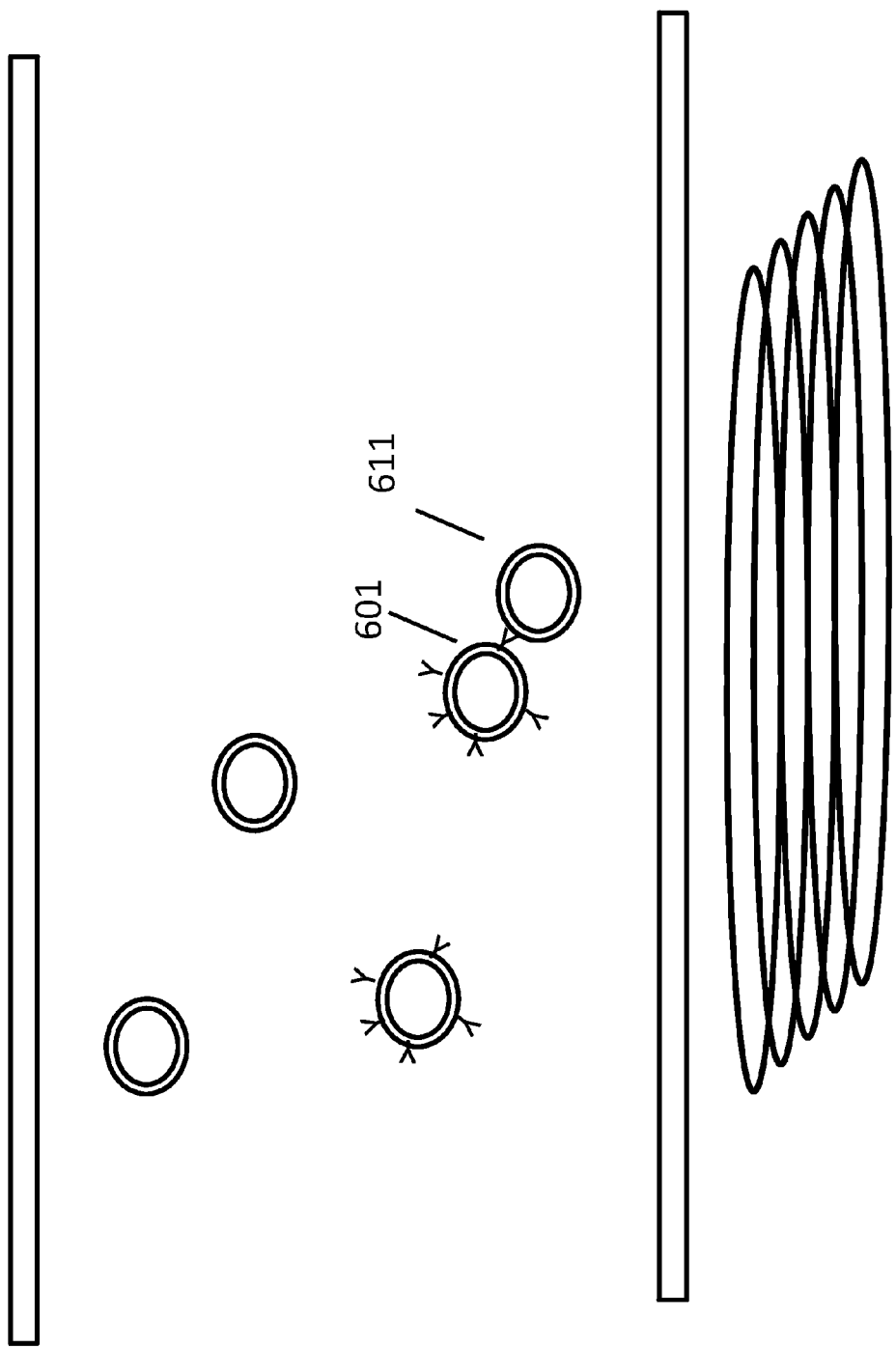
FIG. 6 is an illustration of an embodiment of a micron-sized particle that has attached on part of its exterior at least one type of a biological binder, that will bind to a circulating tumor cell (CTC).

Turning now to FIG. 6, an exemplary embodiment using particles and inductive heating to eliminate circulating tumor cells (CTC) 611. The particle 601 is coated with biding agents such as antibodies that bind to CTCs. The particles are then administered, flow in the blood stream, and bind with CTCs 611. Then induction heating is used at temperatures of above 41 C causing apoptosis or cell death or lysis. Alternatively the particles carry drugs that cause cell death.

According to an embodiment of the present invention, the particles may be monitored with magnetic resonance imaging (MRI) contrast enhancement so that their location within the body is known, that the particles are binding to the plaque, and that the therapy is successful. One of ordinary skill in the art would appreciate that there are numerous usages for MRI in practicing the present invention, and embodiments of the present invention are contemplated for use with any such usage.

Figure 7:
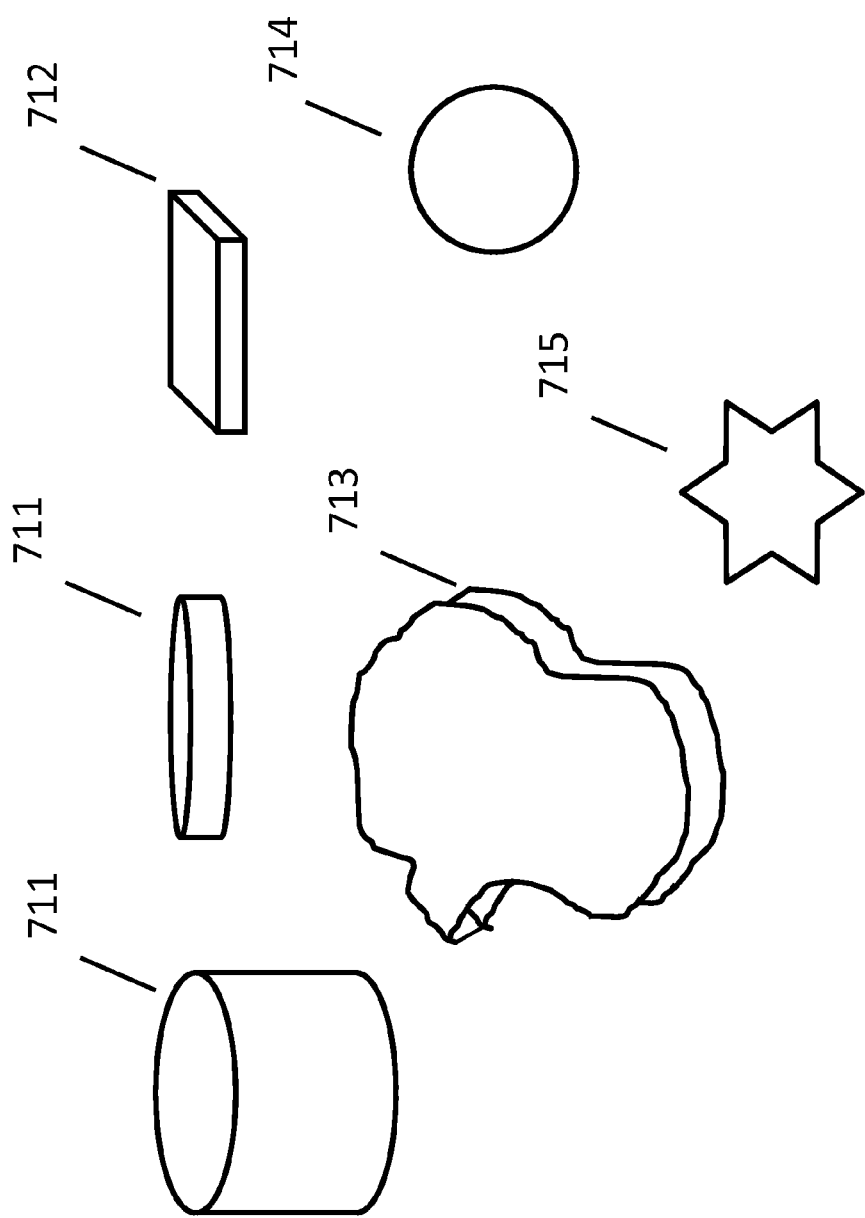
FIG. 7 is an illustration of an embodiment of the various shapes of micron-sized particles.

Turning now to FIG. 7 an exemplary embodiment of particles in varying shapes. Examples of shapes include, but are not limited to, a spherical shape 714, oval shaped, cube, prism, rhombohedron, spheroid, rod, disc, roll, box 712, cylinder 711, or other shape 713 and 715. As an illustrative example the micro-particles may have a cylindrical shape from 10 to 20 micron in height and between 10 micron and 20 micron in diameter. In another example the micro-particle may be 2 micron in height and a 10 micron in diameter. In a preferred embodiment the conductive or metallic or magnetic material is deposited on the edges or at certain parts of the particle in order for it to rotate with an applied alternating magnetic field. The rotation of the particle is such as to allow the particle to slice through matter (such as plaque) thereby reducing the matter or cutting through it.

Turning now to FIG. 8 (a) an illustration of a number of batch fabricated micro-particles that are cylinder 711 shaped. There are several techniques to fabricate micron size particles including patch micro-fabrication techniques. In one embodiment the particles are fabricated using electric discharge machining (EDM) techniques. In EDM material is removed from a piece of metal by quick and frequent current discharges between an electrode and the piece of metal that is being machined, while both are immersed in a dielectric liquid. In another embodiment the particles are fabricated using photo-etching where a photographically prepared mask protects the metal design while the remaining area is chemically etched. These particles can be encapsulated with a polymer such as PDMS, parylene, polyimide, SU-8 or other polymer. Other methods for fabrication include the sol-gel process (a wet-chemical technique) and others. One of ordinary skill in the art would appreciate that there are numerous techniques that could be utilized to manufacture the particles, and embodiments of the present invention are contemplated for use with any such technique.

Turning now to FIG. 8 (b) an illustration of fabrication process steps. The particles can be fabricated by surface or bulk micromachining. In one embodiment one mask is used with the desired pattern. A simple fabrication process includes the following steps. First a sacrificial layer is deposited and patterned such as a metal (for example titanium) on a silicon wafer with a thin silicon oxide layer on top 801. This step is followed by deposition and patterning (by spinning or evaporation or other technique) of an insulating material such as a polymer (examples include parylene, polyimide, SU-8, PDMS) 802. Then a conductive material is deposited and patterned (by evaporation, sputtering or other technique) 803 on top of the insulating layer. In 803 a metal such as chrome may be used between the metal of choice to promote adhesion. For example chrome or titanium may be used the following way: chrome 10 nm, metal of choice such as 1 micron iron, gold, etc., chrome 10 nm. Then this is followed by the optional deposition and patterning of a top insulating layer 804. An optional thin layer of metal may be included on top of the second insulating layer 804 to be used for coating chemistry. For example a thin film of gold of 5 nm (typically chrome/gold with thickness 10 nm/250 nm) can be used. Finally the particles are release 805. For example for 805 a 5% HF for 10 minutes followed by 20 minutes of HF can be used for releasing the particles.

According to an embodiment of the present invention, the surface or part of the surface (also called substrate) of the particle is treated or coated with anti-fouling or patterned to avoid same particles aggregation or biofouling. In a preferred embodiment, the particle is coated with organic polymers with low friction and low surface energies resulting in a hydrophobic surface examples of which include, but are not limited to, fluoropolymers, silicone coatings, polydimethylsiloxane (PDMS), polyvinyl chloride (PVC), high-density polyethylene and polymethylmethacrylate (plexiglas). In another embodiment the surface contains hydrophobic patterns. Alternatively, hydrophilic coatings are used for example zwitterions, such as glycine betaine, sulfobetaine etc. In an advantageous embodiment one of the above materials and patterns are part of (and integrated with) the fabrication process described above or any other fabrication process used to produce particles. One of ordinary skill in the art would appreciate that many materials might be used to coat the particles, and embodiments of the present invention are contemplated for use with any such coating.

Figure 9:
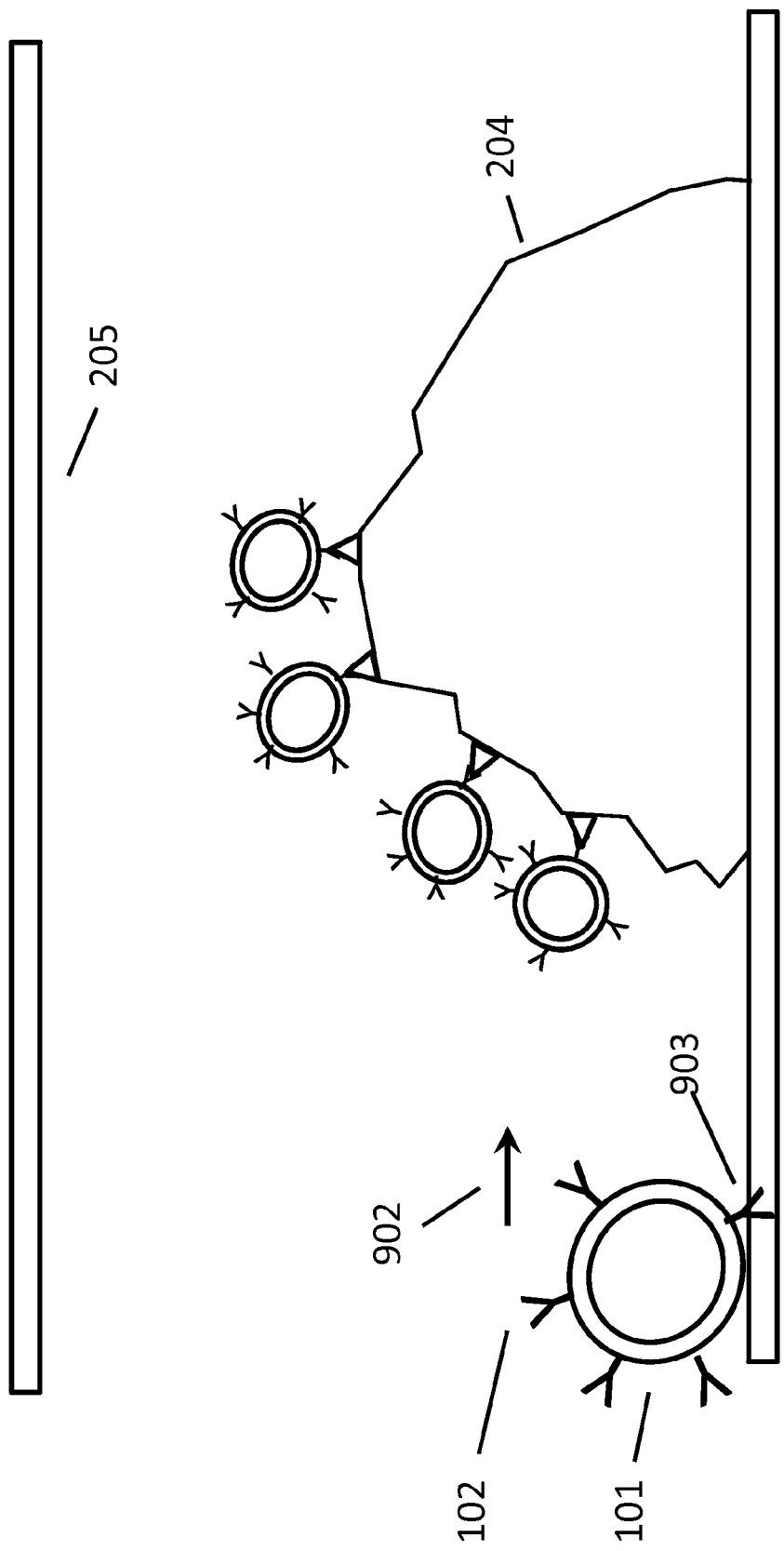
FIG. 9 is an illustration of an embodiment of micron-particles that have attached to them at least two different biological binders, at least one for rolling adhesion and at least one for stationary adhesion.

Turning now to FIG. 9, an exemplary embodiment of micro-particles that have attached to them at least two different biological binders simulating the behavior of leukocytes cells and platelets (when blood clots are formed). The direction of flow and particle 902 is shown and well as the antibody for rolling adhesion 903. The micro-particles are designed and prepared to simulate the movement of leukocytes extravasation out of the circulatory system to repair damage or inflammation. Like leukocytes, the micro-particles are prepared so that they have a rolling adhesion and stationary adhesion with at least two adhesion proteins. As an illustrative example the micro-particles are coated with selectins and their ligands 903 to slow down the micro-particle and make it roll on the surface of the blood vessel wall 205 (endothelium cells). In the same example the micro-particle is also coated another adhesion protein, integrin 102. When the micro-particle encounters a plaque site (or blood clot site) integrin (or another biological binder) forms tight adhesion with the site and the micro-particle stops moving. As soon as sufficient particles are attached to the site (at least one particle) inductive heating is used reduce the plaque matter.

In the preferred embodiment a method for the treatment of vascular deposits via the localized application of heat to said vascular deposits is disclosed, this method comprising the steps of: selecting conductive particles ranging in size between 1 micron and 200 micron (FIG. 7, 711-715, FIG. 8, 511, 101); attaching one or more biological binders to said conductive particles (903, 102); wherein said one or more biological binders will cause said conductive particles to bind a vascular deposit; administering said conductive particles to a patient, wherein said conductive particles enter said patient's circulatory system; allowing said conductive particles to bind to said vascular deposit (204); heating said conductive particles, wherein said conductive particles are inductively heated via an alternating magnetic field (305); reducing said vascular deposit, wherein in said vascular deposit is reduced by inductively heating said conductive particles bound to said vascular deposit (FIG. 4). To further specify the embodiment the conductive particles include an outer insulating layer. To further specify the embodiment the conductive particles are magnetic. To further specify the embodiment the conductive particles are administered with an intravenous needle. To further specify the embodiment further comprising the step of extracting said conductive particles from said patient via an extraction area, wherein a magnet is placed at said extraction area causing said conductive particles to aggregate at said extraction area. To further specify the embodiment the conductive particles are inductively heated for 15 minutes at 41-43 degrees centigrade to cause apoptosis. To further specify the embodiment the particles are used for monitoring said vascular deposits with magnetic resonance imaging (MRI) contrast enhancement. To further specify the embodiment the conductive particles have at least one of said one or more biological binders attached for rolling adhesion and at least one of said or one or more biological binders attached for stationary adhesion. To further specify the embodiment conductive particles are micro-fabricated with a manufacturing method selected from a group of manufacturing methods consisting of electric discharge machining, photo-etching, surface micromachining, and bulk micromachining. To further specify the embodiment the conductive particles are comprised of a polymer bottom layer, a middle conductive layer, and a top polymer layer. To further specify the embodiment one or more biological binders is selected from a group of one or more biological binders consisting of antibodies, proteins, and ligands or the like. To further specify the embodiment polymer bottom layer and said top polymer layer are selected from a group of polymers consisting of parylene, polyimide, SU-8, and polydimethylsiloxane (PDMS).

In another embodiment a method for the treatment of a clot via the localized application of heat to said clot is disclosed, the method comprising the steps of: selecting particles ranging in size between 10 micron and 100 micron; attaching one or more biological binders to said particles; wherein said one or more biological binders will cause said particles to bind a clot; administering said particles to a patient, wherein said conductive particles enter said patient's circulatory system; allowing said particles to bind to said clot; heating said particles, wherein said conductive particles are inductively heated via an alternating magnetic field; reducing said clot, wherein in said clot is reduced by inductively heating said particles bound to said clot.

According to an embodiment of the present invention, the same technique, as described above, can be used to attach a micro-particle to infectious disease agents in the blood stream and to circulating tumor cells or tumor cells in the blood stream. For example, a cancer cells penetrates the walls of lymphatic and/or blood vessels and circulates. At one point the cancer cell will rest at a different site and attempt to re-penetrate the vessel or walls to form a metastatic tumor. Circulating rolling micro-particles with appropriate coating compounds detect the cancer cell as it adheres to the new site and attach to the cell. These micro-particles can then either carry an additional (chemical or biological) material that attacks the cancer cell or are inductively heater in order to lyse or kill or destroy or disable it. One of ordinary skill in the art would appreciate that various afflictions could be treated through the use of micro-particles and induction heating, and embodiments of the present invention are contemplated for treating any such affliction.

The features and advantages of the present invention described in the embodiments are presented for illustrative purposes only and should not be construed to limit the scope of the invention. Many modifications and variations of these embodiments are possible. To illustrate, one can shrink or alter the dimensions and shape of the particle. One or two dimensions may be in the submicron range. None of these figures is drawn to scale. In addition, some of the micro-particles may be drawn larger than the rest to better illustrate their characteristics and features.

While the invention has been thus described with reference to the embodiments, it will be readily understood by those skilled in the art that equivalents may be substituted for the various elements and modifications made without departing from the spirit and scope of the invention. It is to be understood that all technical and scientific terms used in the present invention have the same meaning as commonly understood by one of ordinary skill in the art to which this invention belongs.

The invention claimed is:

1. A method for the treatment of vascular deposits via the localized application of heat to said vascular deposits, said method comprising the steps of:
   selecting conductive particles ranging in size between 1 micron and 200 micron;
   attaching one or more biological binders to said conductive particles; wherein said one or more biological binders will cause said conductive particles to attach to a vascular deposit;
   administering said conductive particles to a patient, wherein said conductive particles enter said patient's circulatory system;
   allowing said conductive particles to attach to said vascular deposit through the biochemical interaction between said biological binders and said vascular deposit;
   heating said conductive particles, wherein said conductive particles are inductively heated via an alternating magnetic field;
   reducing said vascular deposit through the transfer of heat from said conductive particles bound to said vascular deposit.

2. The method of claim 1, wherein said conductive particles include an outer insulating layer.

3. The method of claim 1, wherein said conductive particles are magnetic.

4. The method of claim 1, wherein said conductive particles are administered with an intravenous needle.

5. The method of claim 1, further comprising the step of extracting said conductive particles from said patient via an extraction area, wherein a magnet is placed at said extraction area causing said conductive particles to aggregate at said extraction area.

6. The method of claim 1, wherein said conductive particles are inductively heated for 15 minutes at 41-43 degrees centigrade to cause apoptosis.

7. The method of claim 1, further comprising the step of monitoring said vascular deposits, wherein said conductive particles are used for monitoring said vascular deposits with magnetic resonance imaging (MRI) contrast enhancement.

8. The method of claim 1, wherein said conductive particles have at least one of said one or more biological binders attached for rolling adhesion and at least one of said or one or more biological binders attached for stationary adhesion.

9. The method of claim 8, wherein said one or more biological binders is selected from a group of one or more biological binders consisting of antibodies, proteins, and ligands.

10. The method of claim 1, wherein said conductive particles are micro-fabricated with a manufacturing method selected from a group of manufacturing methods consisting of electric discharge machining, photo-etching, surface micromachining, and bulk micromachining.

11. The method of claim 1, wherein said conductive particles are comprised of a polymer bottom layer, a middle conductive layer, and a top polymer layer.

12. The method of claim 11, wherein said polymer bottom layer and said top polymer layer are selected from a group of polymers consisting of parylene, polyimide, SU-8, and polydimethylsiloxane (PDMS).

13. A method for the treatment of a clot via the localized application of heat to said clot, said method comprising the steps of:
  selecting particles ranging in size between 10 micron and 100 micron;
  attaching one or more biological binders to said particles, wherein said one or more biological binders will cause said particles to attach to a clot;
  administering said particles to a patient, wherein said particles enter said patient's circulatory system;
  allowing said particles to attach to said clot through the biochemical interaction between said biological binders and said clot;
  heating said particles, wherein said particles are inductively heated via an alternating magnetic field; and
  reducing said clot, wherein said clot is reduced by inductively heating said particles bound to said clot.

14. The method of claim 13, wherein said particles include an outer insulating layer.

15. The method of claim 13, wherein said particles are magnetic.

16. The method of claim 13, wherein said particles are administered with an intravenous needle.

17. The method of claim 13, further comprising the step of monitoring said vascular deposits, wherein said particles are used for monitoring said vascular deposits with magnetic resonance imaging (MRI) contrast enhancement.

18. The method of claim 13, wherein said particles have at least one of said one or more biological binders attached for rolling adhesion and at least one of said or one or more biological binders attached for stationary adhesion.

19. The method of claim 13, wherein said particles are micro-fabricated with a manufacturing method selected from a group of manufacturing methods consisting of electric discharge machining, photo-etching, surface micromachining, and bulk micromachining.

20. The method of claim 13, wherein said particles are comprised of a polymer bottom layer, a middle conductive layer, and a top polymer layer.

21. The method of claim 13, wherein said one or more biological binders is selected from a group of one or more biological binders consisting of antibodies, proteins, and ligands.

* * * * *